United States Patent
Jacob et al.

(10) Patent No.: US 10,568,599 B2
(45) Date of Patent: *Feb. 25, 2020

(54) MULTIPLE FRAME ACQUISITION FOR EXPOSURE CONTROL IN X-RAY MEDICAL IMAGERS

(71) Applicant: General Electric Company, Schenectady, NY (US)

(72) Inventors: Biju Jacob, Niskayuna, NY (US); Remy Andre Klausz, Yvelines (FR); John Eric Tkaczyk, Niskayuna, NY (US); Emad Abutabanjeh, Waukesha, WI (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 272 days.

This patent is subject to a terminal disclaimer.

(21) Appl. No.: 15/353,423

(22) Filed: Nov. 16, 2016

(65) Prior Publication Data

US 2017/0119336 A1    May 4, 2017

Related U.S. Application Data

(63) Continuation of application No. 14/481,494, filed on Sep. 9, 2014, now Pat. No. 9,526,468.

(51) Int. Cl.
*A61B 6/00* (2006.01)
*G06T 7/254* (2017.01)

(52) U.S. Cl.
CPC ............ *A61B 6/5264* (2013.01); *A61B 6/42* (2013.01); *A61B 6/4208* (2013.01); *A61B 6/4405* (2013.01); *A61B 6/467* (2013.01); *A61B 6/486* (2013.01); *A61B 6/487* (2013.01); *A61B 6/502* (2013.01); *A61B 6/52* (2013.01); *A61B 6/5205* (2013.01); *A61B 6/5229* (2013.01); *A61B 6/5258* (2013.01); *A61B 6/54* (2013.01); *A61B 6/542* (2013.01); *G06T 7/254* (2017.01); *A61B 6/4233* (2013.01); *G06T 2207/10116* (2013.01); *G06T 2207/30024* (2013.01)

(58) Field of Classification Search
CPC ....... A61B 6/42; A61B 6/4208; A61B 6/4233; A61B 6/486; A61B 6/487; A61B 6/502; A61B 6/52; A61B 6/5205; A61B 6/5258; A61B 6/5264; A61B 6/54; A61B 6/542
USPC .................................................... 378/42, 62
See application file for complete search history.

(56) References Cited

U.S. PATENT DOCUMENTS

| | | | | |
|---|---|---|---|---|
| 4,995,064 A * | 2/1991 | Wilson | ............... | H04N 5/3205 348/E5.089 |
| 5,917,882 A * | 6/1999 | Khutoryansky | ......... | A61B 6/08 378/108 |
| 6,459,765 B1 * | 10/2002 | Ganin | ...................... | A61B 6/00 378/108 |
| 6,510,202 B2 * | 1/2003 | Tamura | .................... | A61B 6/06 378/154 |

(Continued)

*Primary Examiner* — Allen C. Ho
(74) *Attorney, Agent, or Firm* — Fletcher Yoder, P.C.

(57) ABSTRACT

According to some embodiments, a method and a system to create a medical image are disclosed. The method comprises receiving a plurality of patient tissue images during an x-ray dose. Furthermore, during the x-ray dose, a determination is made if motion occurred in the plurality of patient tissue images. In a case that no motion is determined, a diagnostic image of the patient tissue comprising the plurality of patient tissue images is created.

13 Claims, 5 Drawing Sheets

(56) References Cited

U.S. PATENT DOCUMENTS

| | | | | |
|---|---|---|---|---|
| 7,103,136 B2* | 9/2006 | Claus | A61B 6/02 | 378/22 |
| 7,142,633 B2* | 11/2006 | Eberhard | A61B 6/482 | 378/62 |
| 7,263,214 B2* | 8/2007 | Uppaluri | G06F 19/321 | 382/128 |
| 7,280,635 B2* | 10/2007 | Toth | A61B 6/032 | 378/108 |
| 7,313,224 B1* | 12/2007 | Saunders | A61B 6/00 | 378/108 |
| 7,327,823 B2* | 2/2008 | Matsuura | A61B 6/032 | 378/8 |
| 7,340,034 B2* | 3/2008 | Hayashida | A61B 6/00 | 378/98 |
| 7,471,767 B2* | 12/2008 | Spahn | G03B 42/02 | 378/101 |
| 7,502,641 B2* | 3/2009 | Breen | A61B 5/0555 | 600/415 |
| 7,508,913 B2* | 3/2009 | Boese | A61B 6/12 | 378/205 |
| 7,551,721 B2* | 6/2009 | Nakaura | A61B 6/504 | 378/98.12 |
| 7,630,751 B2* | 12/2009 | Boese | A61B 6/481 | 600/407 |
| 7,668,290 B2* | 2/2010 | Tanaka | A61B 6/481 | 378/62 |
| 7,787,670 B2* | 8/2010 | Urushiya | A61B 6/032 | 378/11 |
| 7,994,481 B2* | 8/2011 | Yagi | A61B 6/032 | 250/363.09 |
| 8,027,430 B2* | 9/2011 | Nord | A61B 6/04 | 378/62 |
| 8,055,045 B2* | 11/2011 | Kokubun | A61B 6/032 | 378/4 |
| 8,103,075 B2* | 1/2012 | Boese | G06T 19/00 | 378/8 |
| 8,131,050 B2* | 3/2012 | Tamai | A61B 6/4233 | 382/132 |
| 8,260,025 B2* | 9/2012 | Walimbe | A61B 6/5247 | 378/4 |
| 8,345,823 B2* | 1/2013 | Zaiki | A61B 6/464 | 378/62 |
| 8,428,329 B2* | 4/2013 | Miyamoto | G06K 9/4647 | 378/42 |
| 8,463,009 B2* | 6/2013 | Deimling | G06T 7/246 | 382/128 |
| 8,483,358 B2* | 7/2013 | Allison | A61B 6/00 | 378/65 |
| 8,483,456 B2* | 7/2013 | Nagatsuka | A61B 5/08 | 382/128 |
| 8,509,511 B2* | 8/2013 | Sakaguchi | A61B 6/12 | 382/131 |
| 8,515,003 B2* | 8/2013 | Lechsel | A61B 6/03 | 378/4 |
| 8,542,794 B2* | 9/2013 | Miyamoto | A61B 6/00 | 250/354.1 |
| 8,712,177 B2* | 4/2014 | Liao | G06T 11/60 | 382/254 |
| 8,737,713 B2* | 5/2014 | Baumgart | A61B 6/4441 | 382/132 |
| 8,761,471 B2* | 6/2014 | Ozawa | A61B 6/504 | 382/128 |
| 8,837,671 B2* | 9/2014 | Sakai | A61B 6/06 | 378/62 |
| 8,849,388 B2* | 9/2014 | Brodnick | A61B 6/022 | 600/521 |
| 8,891,843 B2* | 11/2014 | Ohishi | A61B 6/032 | 382/128 |
| 9,044,197 B2* | 6/2015 | Richard | A61B 6/544 | |
| 9,165,363 B2* | 10/2015 | Yoshikawa | G06T 7/337 | |
| 9,192,347 B2* | 11/2015 | Wakai | G06F 19/321 | |
| 9,194,965 B2* | 11/2015 | Xu | G01T 1/295 | |
| 9,198,628 B2* | 12/2015 | Shimada | A61B 6/4291 | |
| 9,230,311 B2* | 1/2016 | Bullard | A61B 6/4233 | |
| 9,259,200 B2* | 2/2016 | Mountney | A61B 6/12 | |
| 9,414,773 B2* | 8/2016 | Kabus | A61B 6/5264 | |
| 9,433,393 B2* | 9/2016 | Takemoto | A61B 6/481 | |
| 9,474,464 B2* | 10/2016 | Iwai | A61B 5/061 | |
| 9,480,437 B2* | 11/2016 | Watanabe | A61B 6/022 | |
| 9,492,135 B2* | 11/2016 | Yamato | A61B 6/503 | |
| 9,521,985 B2* | 12/2016 | Liao | A61B 6/12 | |
| 9,526,468 B2* | 12/2016 | Jacob | A61B 6/5264 | |
| 9,541,509 B2* | 1/2017 | Akahori | A61B 6/486 | |
| 9,542,762 B2* | 1/2017 | Okamoto | A61B 6/032 | |
| 9,566,036 B2* | 2/2017 | Kuroki | A61B 6/463 | |
| 9,576,391 B2* | 2/2017 | Ra | A61B 6/503 | |
| 9,629,935 B2* | 4/2017 | Yeh | A61B 6/481 | |
| 9,633,454 B2* | 4/2017 | Lauritsch | G06T 7/0016 | |
| 9,681,849 B2* | 6/2017 | Shimizu | A61B 6/12 | |
| 9,730,665 B2* | 8/2017 | Choi | A61B 6/5264 | |
| 9,730,666 B2* | 8/2017 | Yamagata | G06T 7/215 | |
| 9,801,555 B2* | 10/2017 | Noji | A61B 5/113 | |
| 9,801,602 B2* | 10/2017 | Nagae | A61B 6/5205 | |
| 9,846,947 B2* | 12/2017 | Fujiwara | G06T 7/20 | |
| 9,886,755 B2* | 2/2018 | Fujiwara | G06T 7/0012 | |
| 9,888,888 B2* | 2/2018 | Kobayashi | A61B 6/06 | |
| 9,888,899 B2* | 2/2018 | Shimizu | A61B 6/542 | |
| 9,898,840 B2* | 2/2018 | Klausz | G06T 11/006 | |
| 9,918,685 B2* | 3/2018 | Fujiwara | A61B 5/1121 | |
| 9,925,392 B2* | 3/2018 | Vilsmeier | A61B 6/032 | |
| 9,928,618 B2* | 3/2018 | Lee | A61B 6/06 | |
| 9,949,709 B2* | 4/2018 | Yi | A61B 6/032 | |
| 9,972,088 B2* | 5/2018 | Fujiwara | G06T 7/0016 | |
| 9,999,399 B2* | 6/2018 | Pang | A61B 6/12 | |
| 10,016,175 B2* | 7/2018 | Sakaguchi | A61B 6/5205 | |

* cited by examiner

MULTIPLE FRAME ACQUISITION FOR EXPOSURE CONTROL IN X-RAY MEDICAL IMAGERS

BACKGROUND

Medical imaging, for example mammography, may use low-energy X-rays as part of a diagnostic and a screening tool to examine patient tissue. Mammography, for example, is used for the detection of breast cancer, typically through detection of characteristic masses contained within the patient tissue. X-ray exposure time, during mammography, may be for several seconds.

Mammography requires that the patient tissue being examined be compressed using a dedicated compression unit (e.g., a parallel-plate compression unit) to even out the thickness of the patient tissue which may increase image quality by reducing a thickness of patient tissue that X-rays have to penetrate. However, compression of patient tissue can be painful for a patient and may result in the patient moving and, in turn, moving the patient tissue during imaging.

When the patient tissue moves during imaging, images acquired by mammography may be blurred and unusable for diagnosing the patient tissue. Since, determining if an image is blurred only occurs after the images are taken, and the images are examined by a technician, a patient may have to endure multiple exposures to X-rays until a clear image is obtained.

Therefore, it would be desirable to design a system and method that allows for determining if an image is blurred while the image is being taken.

BRIEF DESCRIPTION

According to some embodiments, a method to create a medical image is disclosed. The method comprises receiving a plurality of patient tissue images during an x-ray dose. Furthermore, during the x-ray dose, a determination is made if motion occurred in the plurality of patient tissue images. In a case that no motion is determined, a diagnostic image of the patient tissue comprising the plurality of patient tissue images is created. Other embodiments are associated with systems and/or computer-readable medium storing instructions to perform any of the methods described herein.

DRAWINGS

DETAILED DESCRIPTION

The present embodiments, as described herein, may relate to a multi-frame acquisition technique to address the above-mentioned problems. Instead of acquiring a single image after a long x-ray exposure window, the proposed system and method may relate to the acquisition of multiple (e.g., several tens) of images during an exposure window (e.g., a period of time when a patient is exposed to a single dose of X-rays). Patient motion may be detected in real time by tracking the images between successive frames and information associated with each image may be used to make intelligent decisions to control X-ray exposure.

Figure 1:
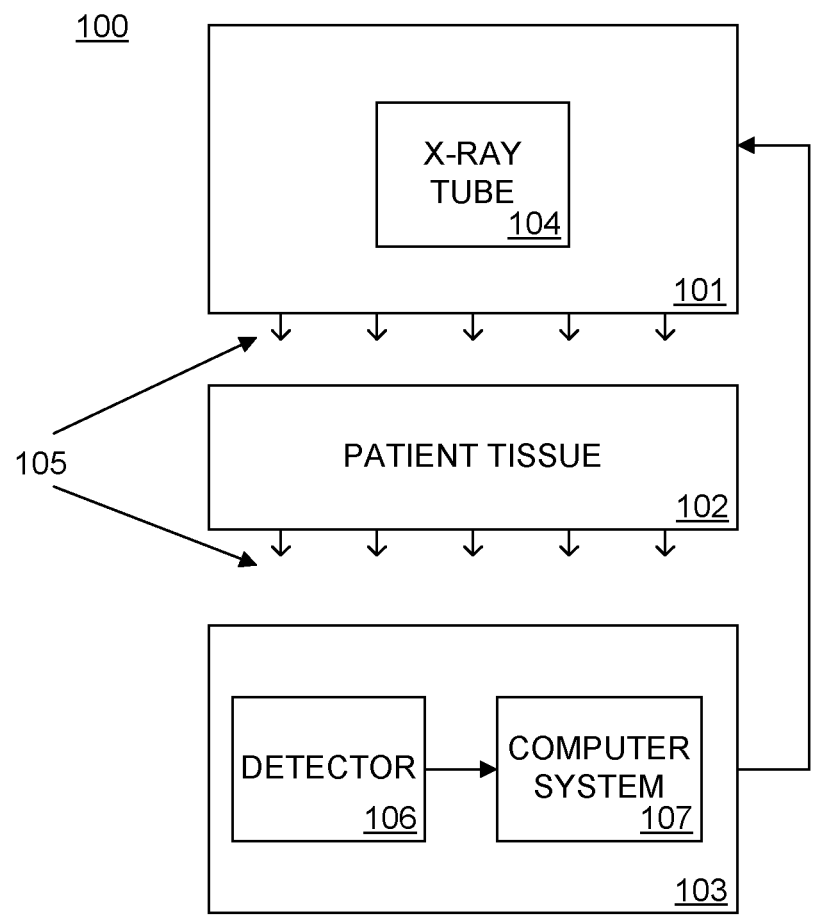
FIG. 1 is a block schematic diagram of a medical imaging system in accordance with some embodiments.
Figure 2:
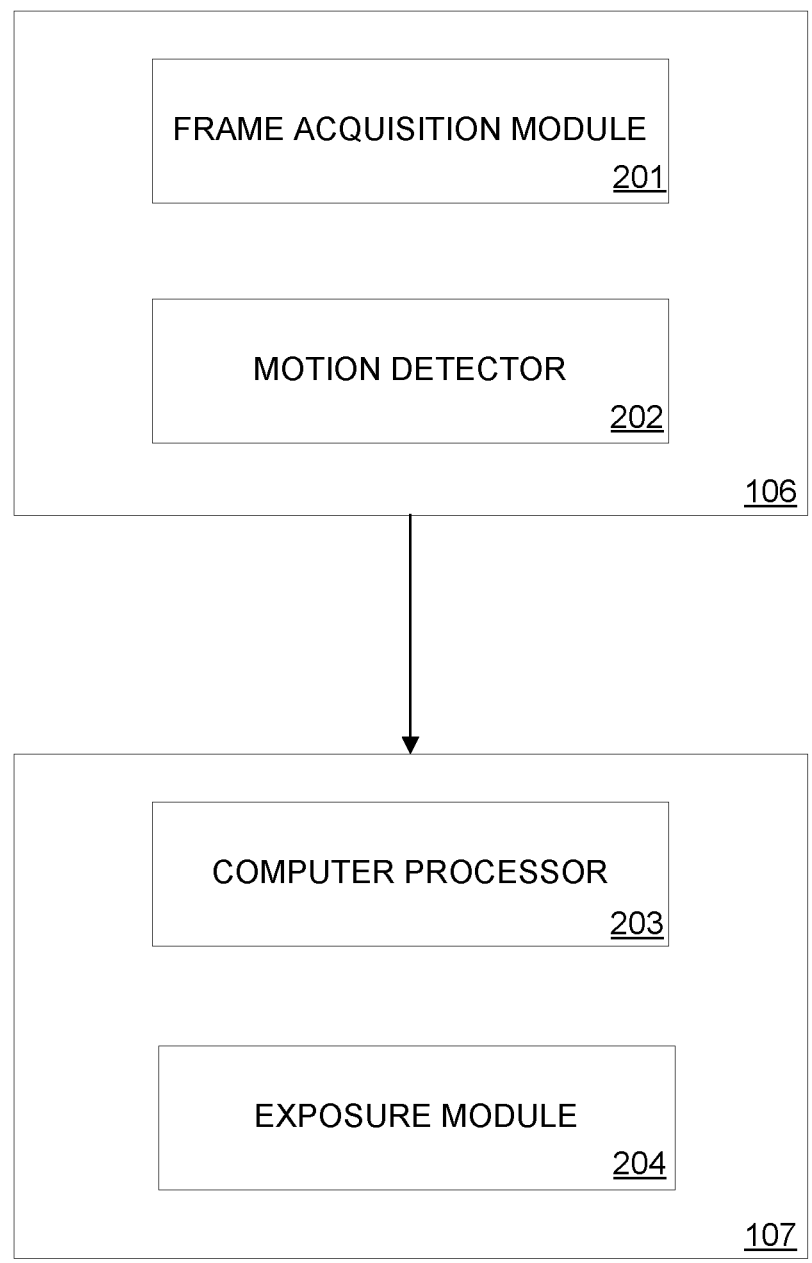
FIG. 2 illustrates components of medical imaging system in accordance with some embodiments.

Referring to FIG. 1 and FIG. 2 a medical imaging system 100 in accordance with some embodiments is shown. The medical imaging system 100 may comprise an X-ray generator 101 to transmit X-rays 105 through patient tissue 102. The X-rays 105 may be received at a receiver 103. The X-ray generator 101 may comprise an X-ray tube 104 to emit X-rays 105. The X-ray tube 104 may comprise a vacuum tube that produces X-rays 105. The patient tissue 102 may comprise an ensemble of similar cells from a same origin, such as, but not limited to, cells associated with breast tissue of a particular patient.

The receiver 103 may comprise a detector 106 and a computer system 107. As illustrated, the detector 106 and the computer system 107 may be internal to the receiver 103, however, in some embodiments, the computer system 107 may be external to the receiver 103. The detector 106 may comprise a semiconductor-based detector, such as a Complementary Metal Oxide Semiconductor ("CMOS") based detector. CMOS is a technology that may be used for X-ray medical imaging detectors because its ultra low electronic noise and fast frame read out capabilities may be used to implement high-performance X-ray detectors.

In some embodiments, the detector 106 may comprise a CMOS X-ray detector that includes an image sensor panel comprising a pixel array. On a top of the image sensor panel a scintillator (not shown) may be disposed. Each pixel in the pixel array may comprise a charge collecting device (e.g., a photodiode) and an electronic circuit to access a signal from the pixel. The pixel array may absorb most of the x-rays and transfer their energy into optical photons that may be efficiently detected by the image sensor underneath. This detection mechanism may be referred to as an "in-direct" mechanism because the X-rays are first converted to optical photons which are in turn detected by the image sensor.

The detector 106 may function as a "camera" that captures X-rays 105. For example, X-ray photons may be converted to electron-hole pairs in the semiconductor based detector and are collected to detect the X-rays 105. The computer system 107 may function as a controller to control the X-ray generator 101 based on input from the detector 106. For example, the detector 106 may determine, during a single dose of X-rays 105, if motion occurred during the capturing of a plurality of patient tissue images and the computer system 107, in response to an input indicating that motion was detected, may manage an X-ray exposure time used to obtain the plurality of patient tissue images as well as manage which of the plurality of patient tissue images to use to create a diagnostic image. For example, in a first case, the computer system 107 may discard images prior to a time when motion is determined by the detector 106 and increase a time of the X-ray dose when the motion is determined at a start of the X-ray dose. In a second case, the computer system 107 may stop the X-ray dose and generate an indication that the X-ray dose was stopped when the motion is determined by the detector at a middle of the X-ray dose. In a third case, the computer system 107 may stop the X-ray dose and discard the images from at time when the motion was determined by the detector 106 when the motion is determined by the detector 106 at an end of the X-ray dose.

Referring to FIG. 2, in some embodiments, the detector 106 may comprise a frame acquisition module 201 and a motion detector 202. Furthermore, the computer system 107 may comprise a computer processor 203 and an exposure module 204 according to some embodiments. Instead of acquiring a single image after an X-ray exposure window, as in conventional systems, the frame acquisition module 201 may acquire multiple (e.g., several tens) of images during a single X-ray dose (e.g., exposure). The motion detector 202 may detect patient motion in real time by tracking an image between successive frames to determine if motion occurred. The information regarding motion may be used by the computer system 107 to make intelligent decision to control X-ray exposure by controlling the X-ray generator 101. In some embodiments, motion may be determined by subtracting a first of a plurality of patient tissue images from a second of the plurality of patient tissue images. In some embodiments, the first and second images of the plurality of patient tissue images may be sequential images. When subtracting images where no motion has occurred, the result of the subtraction may be zero (e.g., each pixel from a first image cancels out a pixel from a second image). However, if motion occurred in one of the images, a result of the subtraction may be a non-zero value (e.g., greater than zero or less than zero). In some embodiments, a degree of motion may be permissible to account for errors associated with imaging variances. In some embodiments, a threshold value may be used instead of zero to compensate for quantum noise associated with the X-ray process. In other embodiments, the comparison between images may be based on comparing a group of summed pixels from each image. Summing groups of pixels may suppress quantum noise associated with the X-ray process. In some embodiments, motion may be detected by analyzing a skin line to determine if the skin line has shifted.

As stated above, the computer system 107 may function as a controller to control the X-ray generator 101 based on input from the detector 106. When the detector 106 determines that motion occurred during the capturing of a plurality of patient tissue images, the computer processor 203 may determine, during the x-ray dose, when the motion occurred and the exposure module 204 may mange the X-ray generator 101 in response to the detection of motion. The computer processor 203 may discard images prior to a time when motion is determined by the detector 106 when the computer processor determines that the motion was at a start of the X-ray dose. In this case, the exposure module 204 may indicate to the X-ray generator 101 to increase a time of the X-ray dose to compensate for the earlier detected motion. The exposure module 204 may stop the X-ray dose being administered by the X-ray generator 101 and the computer processor 203 may generate an indication that the X-ray dose was stopped when the computer processor 203 determines that the motion determined by the detector was during a middle portion of the X-ray dose. The exposure module 204 may stop the X-ray dose being administered by the X-ray generator 101 and the computer processor 203 may discard the images from a time when the motion was determined by the motion detector 202 when the computer processor 203 determines that the motion occurred at an end of the X-ray dose.

Figure 3:
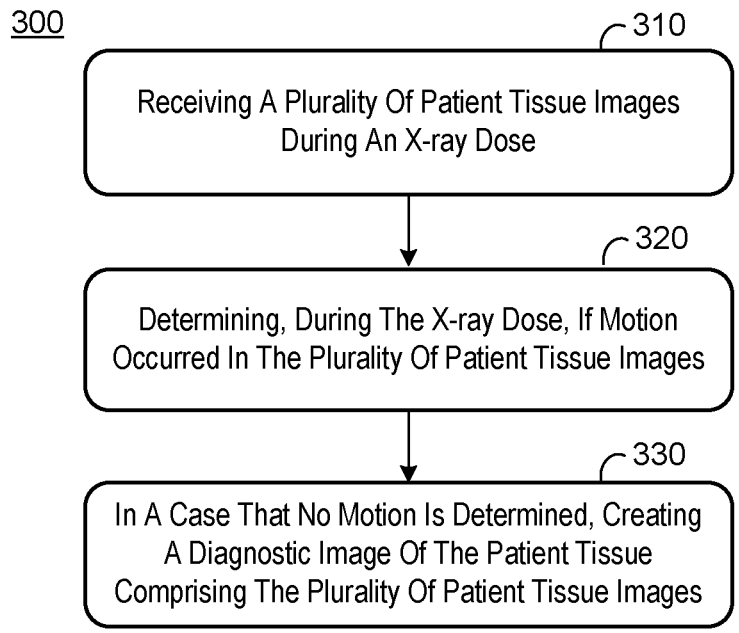
FIG. 3 illustrates a method associated with medical imaging in accordance with some embodiments.

FIG. 3 is a flow chart of a method 300 associated with creating a medical image in accordance with some embodiments. The flow charts described herein do not imply a fixed order to the steps, and embodiments described herein may be practiced in any order that is practicable. Note that any of the methods described herein may be performed by hardware, software, or any combination of these approaches. For example, a computer-readable storage medium (e.g., a non-transitory computer readable storage medium) may store thereon instructions that when executed by a machine result in performance according to any of the embodiments described herein.

At 310, a plurality of patient tissue images captured during an X-ray dose is received. The plurality of patient images may be received at a receiver, such as receiver 103 as described with respect to FIG. 1. The plurality of images may be captured by a detector 106, such as that described with respect to FIG. 2.

For illustrative purposes, and to aid in understanding features of the specification, three examples will now be introduced. These three examples are not intended to limit the scope of the claims. The first example relates to motion being detected in real time during a start of an X-ray dose. The second example relates to motion being detected in real time during a middle of the X-ray dose. The third example relates to motion being detected in real time during an end of the X-ray dose.

Figure 4:
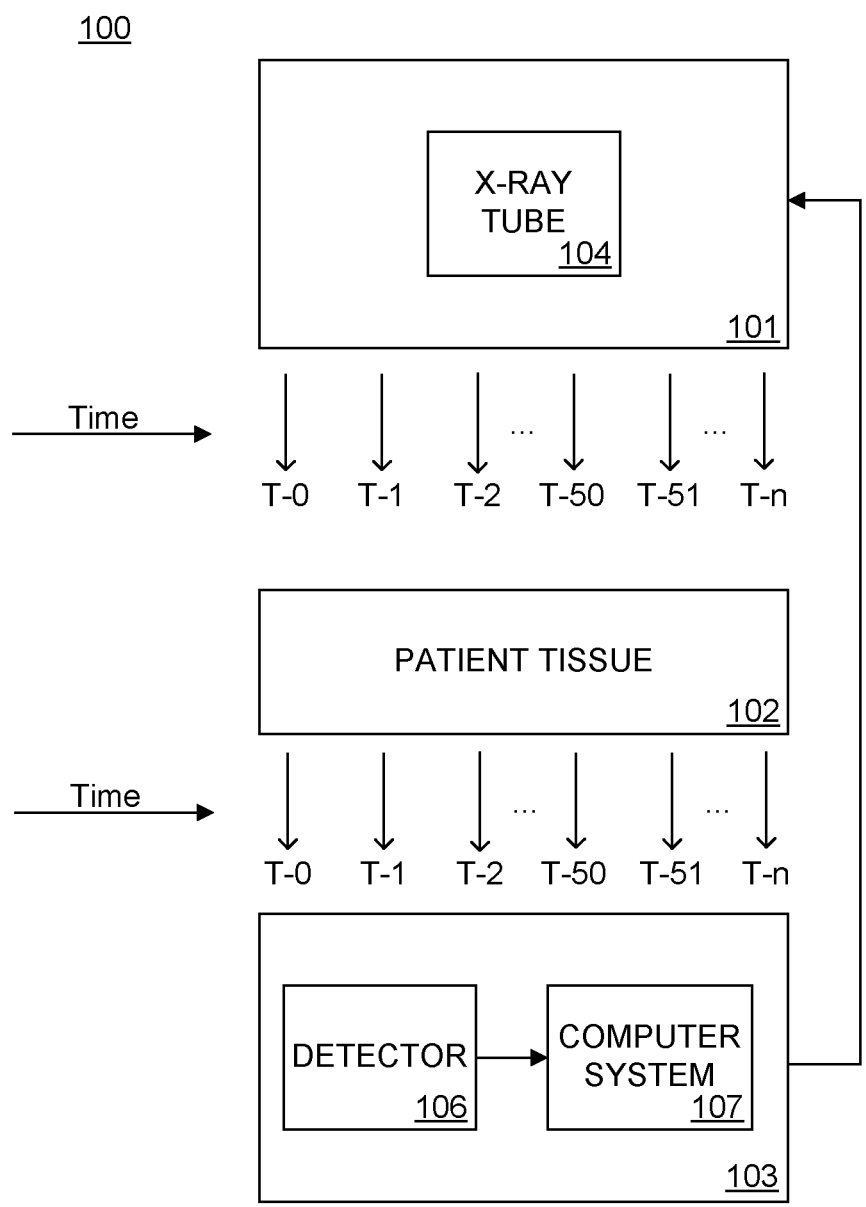
FIG. 4 is a block schematic diagram of a medical imaging system in accordance with some embodiments.

Now referring to FIG. 4, an embodiment of the medical imaging system 100 dispensing a single dose of X-rays 105 over time, as indicated by samples T-0 through T-n, is illustrated. Referring to the first example, a start of an X-ray dose maybe defined, for example, as a first 10% of the time allotted for the X-ray dose (e.g., a first 10% of the received samples). Thus, if the X-ray dose is to last for 2 seconds, the start of the X-ray dose may be defined as 0.2 seconds. The determination of a number of samples that may be captured during the start of the X-ray dose may be based on a sampling rate over a period of 0.2 seconds. The end of the X-ray dose may be defined as a last 10% of the time allotted for the X-ray dose (e.g., a last 10% of the received samples). Thus, if the X-ray dose is to last for 2 seconds, the end of the X-ray dose may be defined as the final 0.2 seconds of the X-ray dose. The determination of a number of samples during the end of the X-ray dose may be based on a sampling rate over a period of 0.2 seconds. The middle of the X-ray dose may be defined as greater than the first 10% of the time allotted for the X-ray dose and less than the last 10% of the time allotted for the X-ray dose. The parameters (e.g., percentages) for defining an end of the X-ray dose and the start of the X-ray dose may be user defined. In the present example, the start of the X-ray dose, as illustrated in FIG. 4, may be between time T-0 and T-2. The end of the X-ray dose, as illustrated in FIG. 4, may be between time T-50 and T-n. The middle of the X-ray dose, as illustrated in FIG. 4, may be between time T-2 and T-50.

Referring back to FIG. 3, at 320 a determination is made, during the X-ray dose, if motion occurred in the plurality of patient tissue images. The determination may be made in real time so that the dose of X-rays can be stopped should motion be detected. By stopping the dose of X-rays in a case when motion is detected, a patient may receive less X-rays than conventional methods. Determining if motion occurred between images may comprise subtracting a previous image from a present image, in real time, to determine if any motion has occurred between the images.

Continuing with the first example, the image at T-0 may be subtracted from the image at T-1. A determination will be made, in real time, if any motion can be detected. Likewise, determinations for the existence of motion will be made for samples associated with the second example and the third example.

At 330, in a case that no motion is determined, a diagnostic image of the patient tissue will be created, the diagnostic image comprising the plurality of patient tissue images. The diagnostic image may comprise a composite of the plurality of images.

However, in a case that motion is detected, a determination will be made as to if the motion occurred at a start of the X-ray dose, a middle portion of the X-ray dose, or at an end of the X-ray dose. In a case that motion is determined at the start of the X-ray dose, the images prior to a time when the motion was determined may be discarded and an amount of time to administer the X-ray dose may be increased. The amount of time to increase the X-ray dose may equal an amount of time when motion was detected at a start of the X-ray dose. For example, if motion was detected at 0.1 second into the X-ray dose, the total exposure time may be extended by 0.1 sec. In a case that motion is determined at the middle of the X-ray dose, the administration of the X-ray dose may be stopped and an indication that the X-ray dose was stopped may be generated and sent to an operator of the X-ray generator. The indication may notify the operator of the X-ray generator that the X-ray exposure may need to be restarted. In a case that motion is determined at the end of the X-ray dose, administration of the X-ray dose may be stopped and the images from at time when the motion was determined may be discarded. In this case, the diagnostic image of the patient tissue may comprise the plurality of patient tissue images taken prior to the time when the motion was determined and a patient may be exposed to less X-rays than conventional systems.

Figure 5:
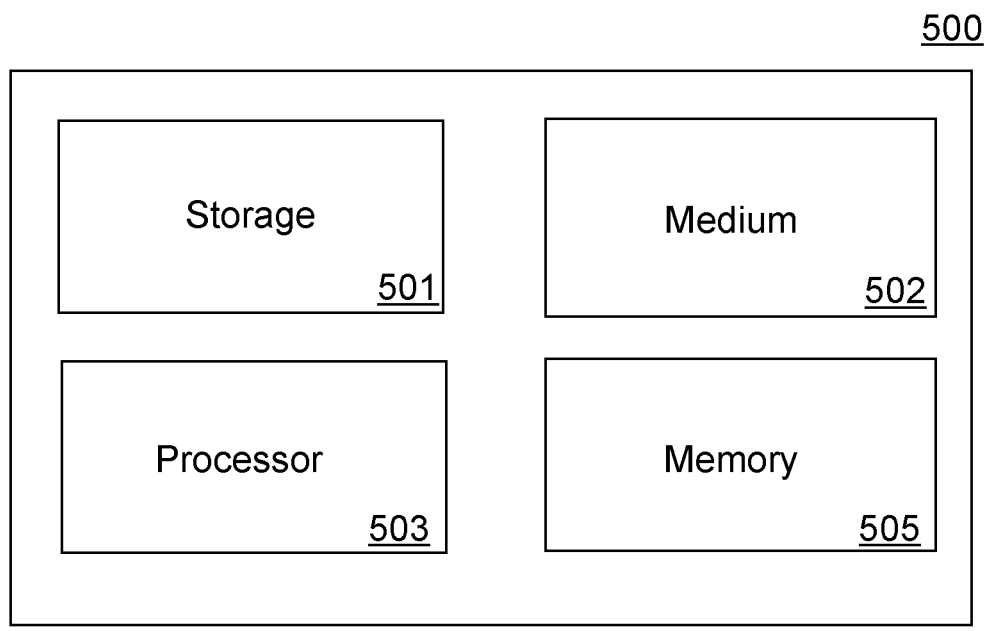
FIG. 5 illustrates components of a computing system in accordance with some embodiments.

Now referring to FIG. 5, an embodiment of a computer system 500 is illustrated. According to some embodiments, the computer system 500 may relate to an X-ray receiver system. The computer system 500 may comprise storage 501, a medium 502, a processor 503 and a main memory 505. According to some embodiments, the computer system 500 may further comprise a digital display port, such as a port adapted to be coupled to a digital computer monitor, television, portable display screen, or the like.

The storage 501 may store information (e.g., including information associated with X-ray exposures). The medium 502 may comprise any computer-readable medium that may store processor-executable instructions to be executed by the processor 503. For example, the medium 502 may comprise a non-transitory tangible medium such as, but is not limited to, a compact disk, a digital video disk, flash memory, optical storage, random access memory, read only memory, or magnetic media.

The processor-executable instructions may be stored in a compressed, uncompiled and/or encrypted format. The processor-executable instructions may furthermore include program elements, such as an operating system, a database management system, and/or device drivers used by the processor 503 to interface with peripheral devices.

The processor 503 may include or otherwise be associated with dedicated registers, stacks, queues, etc. that are used to execute program code and/or one or more of these elements may be shared there between. In some embodiments, the processor 503 may comprise an integrated circuit. In some embodiments, the processor 503 may comprise circuitry to perform a method such as, but not limited to, the method described with respect to FIG. 3.

The processor 503 communicates with the storage 501. The storage 501 may comprise any appropriate information storage device, including combinations of magnetic storage devices (e.g., a hard disk drive), optical storage devices, and/or semiconductor memory devices. The storage 501 may store a program for controlling the processor 503. The processor 503 performs instructions of the program, and thereby operates in accordance with any of the embodiments described herein. For example, the processor 503 may determine when motion occurred in a plurality of patient tissue images.

The main memory 505 may comprise any type of memory for storing data, such as, but not limited to, a Secure Digital (SD) card, a micro SD card, a Single Data Rate Random Access Memory (SDR-RAM), a Double Data Rate Random Access Memory (DDR-RAM), or a Programmable Read Only Memory (PROM). The main memory 505 may comprise a plurality of memory modules.

It is to be understood that not necessarily all such advantages described above may be achieved in accordance with any particular embodiment. Thus, for example, those skilled in the art will recognize that the systems and techniques described herein may be embodied or carried out in a manner that achieves or optimizes one advantage or group of advantages as taught herein without necessarily achieving other advantages as may be taught or suggested herein.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A medical imaging system, comprising:
   an X-ray tube to generate a dose of X-rays;
   a detector to capture a plurality of patient tissue images during the dose of X-rays; and
   a computer system to:
   (i) determine, during the dose of X-rays, if motion occurred during the capture of the plurality of patient tissue images;
   (ii) manage the plurality of patient tissue images;
   (iii) when that motion occurred during the capture of the plurality of patient tissue images, determine if the motion occurred at a start of the dose of X-rays, at a middle of the dose of X-rays, or at an end of the dose of X-rays; and
   (iv) when that motion occurred at the end of the X-ray dose, stopping the X-ray dose and discarding patient tissue images from the plurality of patient tissue images from a time when the motion occurred.

2. The medical imaging system of claim 1, wherein the computer system determines if motion occurred comprises subtracting a first patient tissue image of the plurality of patient tissue images from a second patient tissue image of the plurality of patient tissue images.

3. The medical imaging system of claim 1, wherein when that motion occurred at the middle of the X-ray dose, the computer system stops the X-ray dose and generates an indication that the X-ray dose was stopped.

4. The medical imaging system of claim 1, wherein when that motion occurred at the start of the X-ray dose, discards the patient tissue images from the plurality of patient tissue images from prior to a time when the motion occurred and increases a time of the X-ray dose.

5. The medical imaging system of claim 1, wherein the detector comprises CMOS-based detectors.

6. A method to create a medical image, the method comprising:
   receiving, by a computer system, a plurality of patient tissue images during an X-ray dose;
   determining, during the X-ray dose, if motion occurred in the plurality of patient tissue images;

in a case that motion occurred, determining if the motion occurred at a start of the X-ray dose, at a middle of the X-ray dose, or at an end of the X-ray dose; and when that motion occurred at the end of the X-ray dose, stopping the X-ray dose and discarding patient tissue images from the plurality of patient tissue images from a time when the motion occurred.

7. The method of claim 6, wherein determining if motion occurred comprises subtracting a first patient tissue image of the plurality of patient tissue images from a second patient tissue image of the plurality of patient tissue images.

8. The method of claim 6, further comprising: in a case that motion occurred at the middle of the X-ray dose: stopping the X-ray dose; and generating an indication that the X-ray dose was stopped.

9. The method of claim 6, further comprising: when that motion occurred at the start of the X-ray dose, discarding the patient tissue images from the plurality of patient tissue images from prior to a time when the motion occurred and increasing a time of the X-ray dose.

10. A non-transitory, computer-readable medium storing instructions that, when executed by a computer processor, cause the computer processor to perform a method associated with creating a medical image, the method comprising:

receiving, by a computer system, a plurality of patient tissue images during an X-ray dose; determining, during the X-ray dose, if motion occurred in the plurality of patient tissue images;

in a case that motion occurred, determining if the motion occurred at a start of the X-ray dose, at a middle of the X-ray dose, or at an end of the X-ray dose; and when that motion occurred at the end of the X-ray dose, stopping the X-ray dose and discarding patient tissue images from the plurality of patient tissue images from a time when the motion occurred.

11. The non-transitory, computer-readable medium of claim 10, wherein determining if motion occurred comprises subtracting a first patient tissue image of the plurality of patient tissue images from a second patient tissue image of the plurality of patient tissue images.

12. The non-transitory, computer-readable medium of claim 10, further comprising: in a case when that motion occurred at the middle of the X-ray dose: stopping the X-ray dose; and generating an indication that the X-ray dose was stopped.

13. The non-transitory, computer-readable medium of claim 10, further comprising: when that motion occurred at the start of the X-ray dose, discarding the patient tissue images from the plurality of patient tissue images from prior to a time when the motion occurred and increasing a time of the X-ray dose.

* * * * *